United States Patent
Zhu et al.

(10) Patent No.: US 7,890,171 B2
(45) Date of Patent: *Feb. 15, 2011

(54) SENSORS HAVING PROTECTIVE ELUTING COATING AND METHOD THEREFOR

(75) Inventors: Qingsheng Zhu, Little Canada, MN (US); Ronald W. Heil, Jr., Roseville, MN (US); Mudit Jain, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 627 days.

This patent is subject to a terminal disclaimer.

(21) Appl. No.: 11/738,251

(22) Filed: Apr. 20, 2007

(65) Prior Publication Data

US 2007/0191921 A1 Aug. 16, 2007

Related U.S. Application Data

(63) Continuation of application No. 10/677,144, filed on Sep. 30, 2003, now Pat. No. 7,225,024.

(51) Int. Cl.
*A61N 1/00* (2006.01)
(52) U.S. Cl. ..................................................... 607/22
(58) Field of Classification Search ................ 600/333, 600/341, 310, 325; 607/22, 17, 36, 120, 607/129, 60, 9; 424/419; 427/2.1; 604/264, 604/890.1; 514/365
See application file for complete search history.

(56) References Cited

U.S. PATENT DOCUMENTS

| | | | |
|---|---|---|---|
| 3,056,727 A * | 10/1962 | Allais et al. ................. | 514/174 |
| 3,087,860 A * | 4/1963 | Endicott ..................... | 424/419 |
| 4,023,562 A | 5/1977 | Nynecek et al. | |
| 4,407,296 A | 10/1983 | Anderson et al. | |
| 4,589,418 A | 5/1986 | Gopikanth | |
| 4,750,494 A | 6/1988 | King | |
| 4,791,935 A | 12/1988 | Baudino et al. | |
| 4,807,632 A | 2/1989 | Liess et al. | |
| 4,815,469 A | 3/1989 | Cohen et al. | |
| 4,819,661 A | 4/1989 | Heil, Jr. et al. | |
| 4,819,662 A | 4/1989 | Heil, Jr. et al. | |
| 4,900,136 A | 2/1990 | Goldburt et al. | |
| 5,058,586 A | 10/1991 | Heinze | |
| 5,156,148 A | 10/1992 | Cohen | |
| 5,267,564 A | 12/1993 | Barcel et al. | |
| 5,324,324 A | 6/1994 | Vachon et al. | |
| 5,462,976 A * | 10/1995 | Matsuda et al. ............... | 522/74 |
| 5,466,254 A | 11/1995 | Helland | |
| 5,556,421 A * | 9/1996 | Prutchi et al. ................ | 607/36 |
| 5,820,917 A * | 10/1998 | Tuch ........................... | 427/2.1 |

(Continued)

OTHER PUBLICATIONS

"Prosecution File History for U.S. Appl. No. 10/677,144", 92 pgs.

*Primary Examiner*—George Manuel
*Assistant Examiner*—Robert N Wieland
(74) *Attorney, Agent, or Firm*—Faegre & Benson LLP

(57) ABSTRACT

An apparatus includes an implantable device, such as a chronically implantable device that has a device body. One or more chemical sensors are coupled with the device body. A drug eluting substance is disposed at a location including at least one of on, directly adjacent, or near the one or more chemical sensors, where the drug eluting substance prevents fibrotic growth on the one or more chemical sensors.

25 Claims, 4 Drawing Sheets

U.S. PATENT DOCUMENTS

| | | |
|---|---|---|
| 5,902,329 A | 5/1999 | Hoffmann et al. |
| 5,931,862 A | 8/1999 | Carson |
| 6,125,290 A * | 9/2000 | Miesel ............... 600/325 |
| 6,144,869 A | 11/2000 | Berner et al. |
| 6,212,416 B1 * | 4/2001 | Ward et al. ............ 600/345 |
| 6,234,973 B1 | 5/2001 | Meador et al. |
| 6,304,786 B1 | 10/2001 | Heil, Jr. et al. |
| 6,331,163 B1 | 12/2001 | Kaplan |
| 6,671,562 B2 | 12/2003 | Osypka et al. |
| 6,689,803 B2 * | 2/2004 | Hunter ............... 514/365 |
| 7,096,064 B2 * | 8/2006 | Deno et al. ............ 607/9 |
| 7,225,024 B2 | 5/2007 | Zhu et al. |
| 7,662,864 B2 * | 2/2010 | Kanamathareddy et al. ........ 514/772.5 |
| 2003/0153901 A1 | 8/2003 | Herweck et al. |
| 2005/0027283 A1 * | 2/2005 | Richard et al. ........ 604/890.1 |
| 2007/0299409 A1 * | 12/2007 | Whitbourne et al. ...... 604/264 |

* cited by examiner

SENSORS HAVING PROTECTIVE ELUTING COATING AND METHOD THEREFOR

CROSS-REFERENCE TO RELATED APPLICATION

This application is a continuation of U.S. patent application Ser. No. 10/677,144, filed on Sep. 30, 2003, which has now issued as U.S. Pat. No. 7,225,024, the specification of which is incorporated herein by reference.

TECHNICAL FIELD

The present invention relates generally to implantable devices. More particularly, it pertains to implantable devices with sensors.

BACKGROUND

Sensors are used for monitoring and/or recording of various human physical, chemical and/or physiological parameters. For example a sensor can be included with a medical device such as a pacemaker, and can be permanently implanted in a specific location within the human body. This sensor is used to monitor, and sometimes chronically monitor, certain physical and/or physiological parameters of the subject in which it has been implanted.

While it is helpful to gain information chronically from a sensor implanted within a patient, one limitation is the susceptibility of the sensor to conditions and risks associated with implanting a device within the body. For example, some sensors have fragile components that are sensitive to pressure. As a result, there is a risk that the sensor will be damaged during insertion, deployment and/or positioning of the implantable device. Damage to the sensor could result in poor performance or non-operability of the sensor.

Another concern with including sensors on implantable devices is the erosion of material when it is implanted in a patient and exposed for a prolonged period of time to bodily fluids and other naturally occurring agents inside the patient. In yet another concern with sensors, is the build-up of fibrotic growth on the sensor during the prolonged period of exposure to bodily fluids. The fibrotic growth on the sensor can lead to dampening of an implantable sensor response or reduction in signal strength, potentially affecting the ability to monitor.

What is therefore needed is an implantable sensor that overcomes the issues related to fibrotic growth on or affecting the sensor.

SUMMARY

An apparatus includes an implantable device, such as a chronically implantable device that has a device body. One or more chemical sensors are coupled with the device body. A drug eluting substance is disposed at a location including at least one of on, directly adjacent, or near the one or more chemical sensors, where the drug eluting substance prevents fibrotic growth on the one or more chemical sensors.

Several options for the apparatus are as follows. For example, in one option, the drug eluting substance includes a drug mixed with a polymeric binding. In another option, the device body includes a cavity, where the cavity is disposed adjacent the one or more chemical sensors, and the drug eluting substance is disposed within the cavity. In yet another option, the drug eluting substance is coated on the chemical sensor. Several other options exist, as discussed further below and/or as illustrated further in the drawings.

In another option, an implantable device with a device body is provided. The device includes one or more blood monitoring sensors coupled with the device body, and a drug eluting substance is disposed on the one or more blood monitoring sensors, where the drug eluting substance prevents fibrotic growth on the one or more blood monitoring sensors.

Some of the options for the implantable device are as follows. For instance, in one option, the one or more blood monitoring sensors is a glucose sensor, or a sensor that monitors one or more of bicarbonate, blood urea nitrogen (BUN), brain naturetic peptide (BNP), calcium, chloride, osmolarity, potassium, renin, or sodium. In yet another option, the device body includes a cavity, with a pre-compressed drug substance that is shaped to fit within the cavity. Optionally, the pre-compressed drug substance includes a drug compressed with a starch.

A method includes providing a chronically implantable device body, coupling a chemical sensor with the implantable device body, disposing a drug eluting substance on a portion of the chronically implantable device body, and disposing the drug eluting substance on a portion of the chronically implantable device body includes disposing the drug eluting substance on, near, or directly adjacent to the chemical sensor. The method further includes preventing fibrotic growth with the drug eluting substance.

Several options for the method are as follows. For instance, in one option, disposing the drug eluting substance includes painting a drug on the chronically implantable device body. In one option, the drug that is painted on the device body is compounded to immobilize the drug in a thin layer. In one embodiment of this drug paint, an active drug substance is mixed into an uncured polymeric phase that is subsequently applied (painted, sprayed, dip-coated, etc) onto a surface. Upon exposure to the fluids of the body, the active drug substance would dissolve from the surface film and be delivered to the tissue.

In another option, disposing the drug eluting substance includes filling a cavity of the chronically implantable device body with the drug eluting substance. In yet another option, the method further includes binding the drug eluting substance with a polymer. Several other options exist, as discussed further below and/or as illustrated further in the drawings.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

An apparatus includes an implantable device, such as a chronically implantable device that has a device body. One or more chemical sensors are coupled with the device body. A drug eluting substance is disposed at a location including at least one of on, directly adjacent, or near the one or more chemical sensors, where the drug eluting substance prevents fibrotic growth on the one or more chemical sensors. The apparatus will now be described in greater detail.

Figure 1:
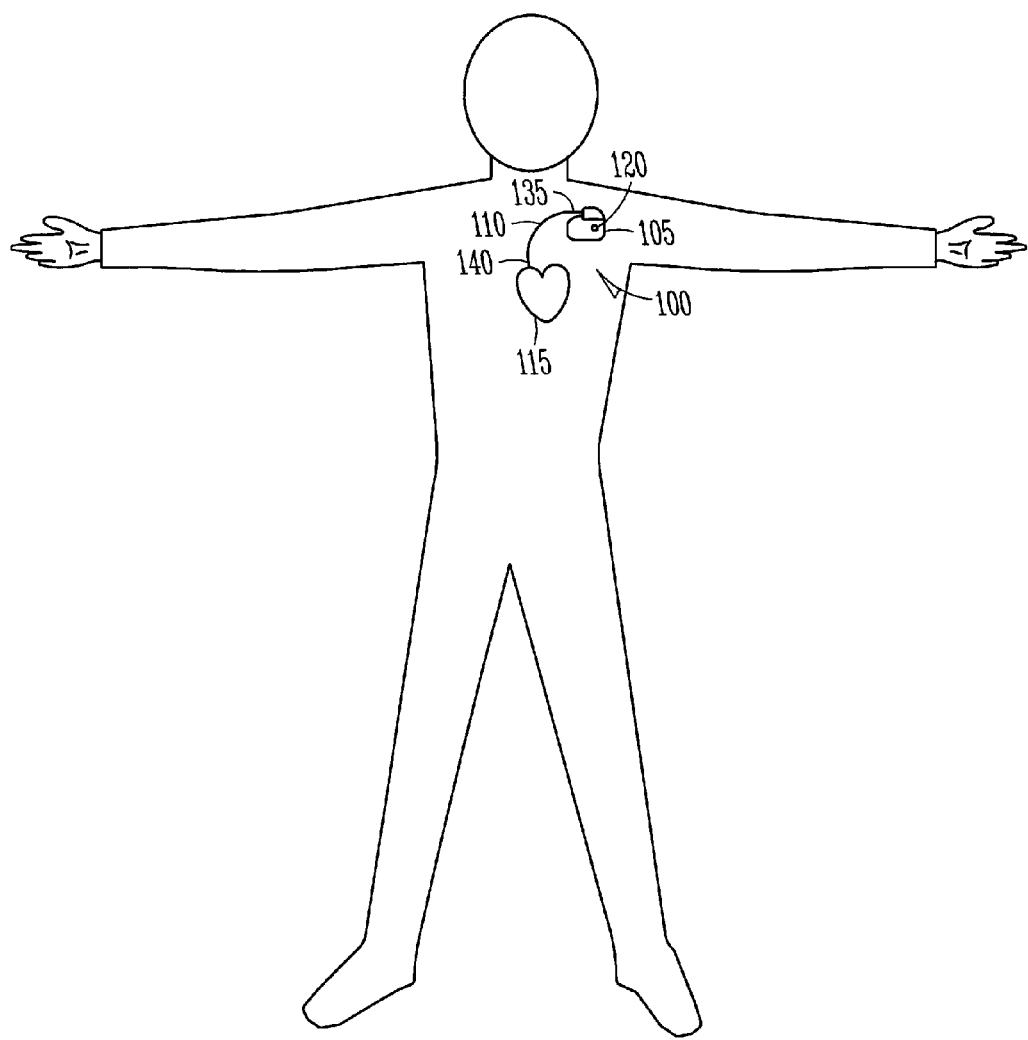
FIG. 1 is a schematic drawing illustrating portions of an implantable device as constructed in accordance with one embodiment.

FIG. 1 is a schematic drawing illustrating generally, by way of example, but not by way of limitation, one embodiment of an implantable device, such as a chronically implantable device that is implanted within a patient over an extended period of time. In one example, the implantable device 100 includes portions of a cardiac rhythm management system. The implantable device 100 includes an implantable cardiac rhythm management device 105, which is coupled via an intravascular endocardial lead 110 to a heart 115 of a human or other patient. The endocardial lead 110 assists in conducting electrical signals between the cardiac rhythm management device 105 and the heart 115. The lead 110 includes a proximal end 135, which is coupled to device 105, and a distal end 140, which is coupled on or about one or more portions of heart 115. The implantable device 100 further includes one or more chemical sensors thereon. For example, in one option the one or more chemical sensors 120 are coupled with the cardiac rhythm management device 105. The chemical sensors 120 and coatings, therapeutic agents, etc. will be described in further detail below.

Figure 2:
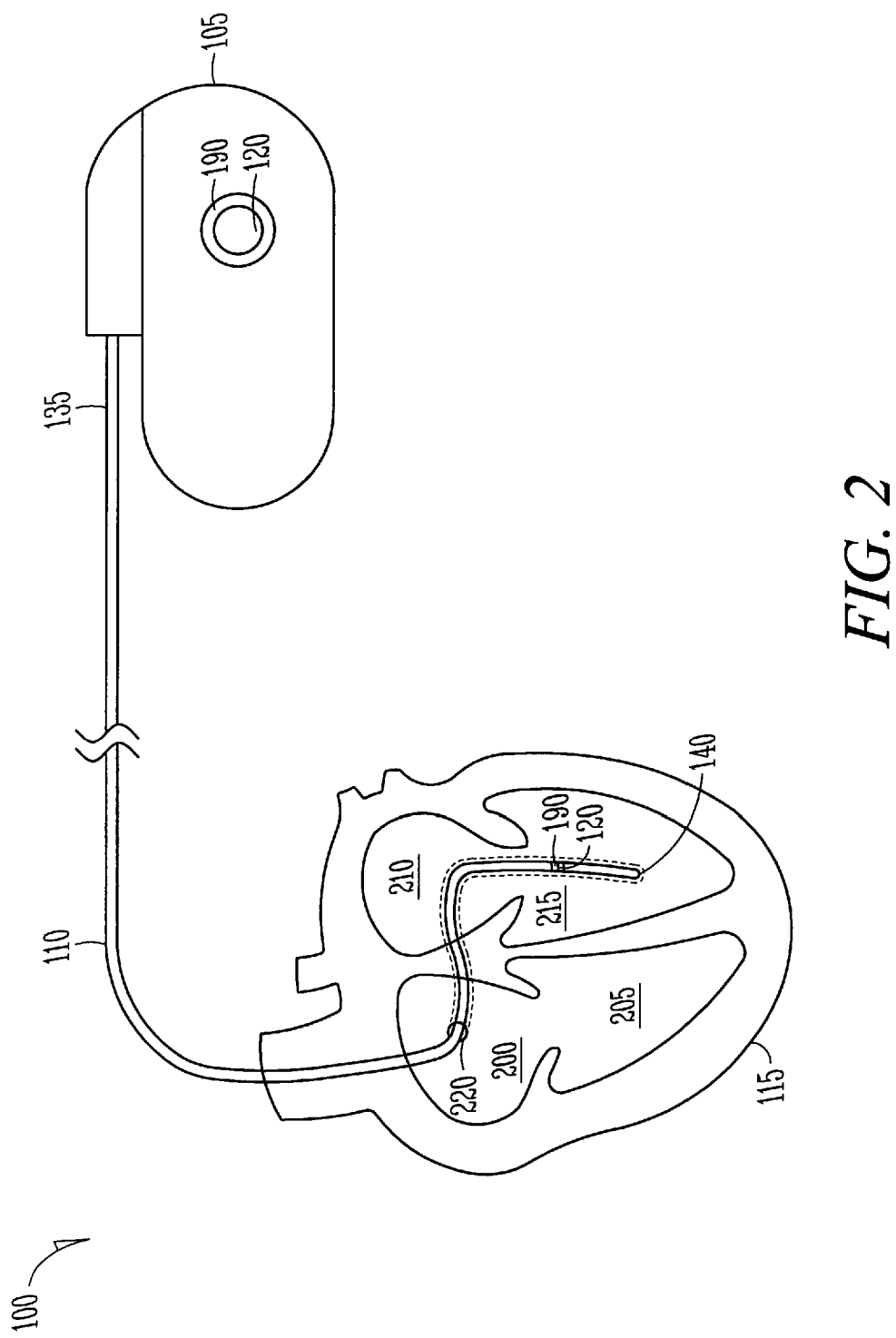
FIG. 2 is a drawing illustrating an implantable device as constructed in accordance with another embodiment.

FIG. 2 is a schematic drawing illustrating generally, by way of example, but not by way of limitation, one embodiment of an exemplary disposition of distal portions of lead 110. FIG. 2 illustrates chambers of heart 115, including a right atrium 200, a right ventricle 205, a left atrium 210, and a left ventricle 215. In one option, a distal end 140 of the lead 110 is transvenously guided into right atrium 200, through a coronary sinus 220, and into a great cardiac vein. This is one example of a lead 110 disposition that is useful for delivering pacing and/or defibrillation energy to the left side of heart 115, such as for treatment of congestive heart failure (CHF) or other cardiac disorders requiring therapy delivered to the left side of heart 115. Other possible dispositions of distal portions of endocardial lead 110 include insertion into right atrium 200 and/or right ventricle 205, or transarterial insertion into the left atrium 210 and/or left ventricle 215. Other chronically implantable devices are suitable as well.

In one option, the lead 110 and/or the cardiac rhythm management device 105 further includes a sensor 120, such as a chemical sensor thereon. In one example, a miniature sensor or multiple miniature sensors can be placed on the lead 110 for monitoring and optimizing therapy. In one option, the sensor 120 is coupled with a device body.

The at least one sensor 120 monitors, in one option, chemical substances present within the blood or tissue in which the implantable device 100 is implanted. For example, the at least one sensor 120 monitors one or more of the following: bicarbonate, blood urea nitrogen (BUN), brain naturetic peptide (BNP), calcium, chloride, C-reactive peptide (CRP), creatine phosphokinase (CPK), creatinine, glucose, osmolarity, $pCO_2$, pH, $pO_2$, potassium, renin, or sodium.

The implantable device 100 further includes at least one drug eluting substance 190 that is disposed at a location that is on, directly adjacent, or near the one or more chemical sensors. In one option, the drug eluting substance 190 is coated on the sensor 120. In another option, the drug eluting substance 190 is disposed around the outer perimeter of the at least one sensor 120.

Figure 3:
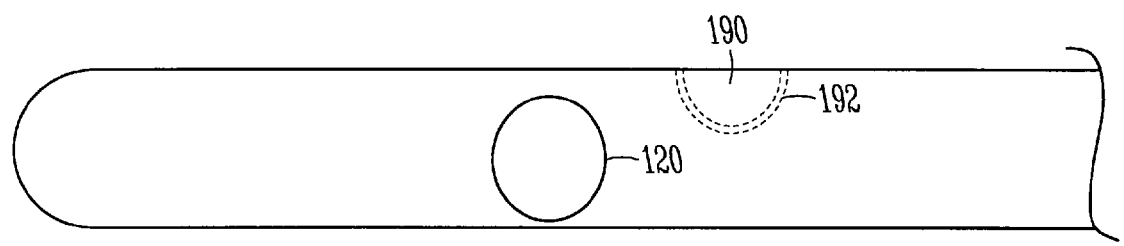
FIG. 3 is a side elevational view illustrating a portion of an implantable device as constructed in accordance with another embodiment.

FIG. 3 illustrates another example for the implantable device 100. The device body, in one option, includes a cavity 192 therein. The one or more cavities 192, in one option, are disposed near, or directly adjacent to the at least one sensor 120. In one option, the one of more cavities have a shape such as a ring that completely encircles a perimeter of the device body at a location that is adjacent and, in one option, on one side of the sensor. In another option, the cavities are shaped so as to form an arc that partially or completely surrounds a perimeter of the sensor. In another option, the sensor is disposed within a recess of the device body. The one or more cavities are tunneled into the wall of the recess and, and optionally are tunneled to a location that is above an active sensor element. In another option, a plurality of cavities are disposed within the device body, and are optionally disposed in an annular ring that, in another option, forms the wall of the recess.

The drug eluting substance 190 is formed into a shape that, in one option, has a preformed shape that fits within the cavity 192. In another option, the drug eluting substance 190 is malleable and can be disposed within the cavity 192, and further processed, for example, by curing or hardening with other agents.

The drug eluting substance 190 can be formed in several different manners. For example, in one option, the drug eluting substance 190 includes a drug mixed with a polymeric binding. Examples of polymers include, but are not limited to silicone, polyurethane, and polyethylene. For example, the polymeric binder is dissolved in an appropriate volatile agent such as tetrahydrofuran, FREON®, hexane, heptane, methylene chloride, or the like, with the drug subsequently added to the polymer solution. Due to the high vapor pressures of these solvents, they will quickly evaporate to leave the drug in a polymeric binder.

In another option, the drug eluting substance 190 includes a drug eluting matrix that elutes drugs over time. In one example, the drug eluting matrix is a steroid compounded with an uncured silicone rubber. Upon curing, the steroid becomes incorporated into the hardened polymeric binder. The curing process, in one option, is performed within a mold to produce a desired matrix shape. In another option, the curing process is performed to produce a matrix sheet, rod, tube, or other shape which can be cut or trimmed into a final desired shape. In one example, such as for a pacing lead, a rod or a tube of dexamethasone acetate-in-silicone rubber is cut to form a plug or a ring, respectively. In yet another option, the drug eluting substance 190 is a drug esterificated drug.

The drugs of the drug eluting substance 190, and/or the drug eluting substance 190 can be modified to affect flow rates, dissolvability, etc. For example, in one option, the drug eluting substance 190 includes a drug mixed with a polymeric binding.

In one option, the drug eluting substance if formed by pressure molding used to compress, for example, a platelet inhibitor drug to form a tablet-like capsule. In one option, the capsule is formed of 100% of drugs that begin eluting on contact with blood. In another option, the capsule is formed of less than 100%. For example, in another option, a drug in combination with starch and/or manitol are formed into a capsule by pressure molding the combination. In one option, the capsule, such as the combination capsule, dissolves at a slower pace than the capsule formed of 100 percent of a drug or therapeutic agent, or higher concentrations of drugs or therapeutic agents.

The drug eluting substance 190 includes therapeutic agents that prevent fibrotic growth on the sensor, or near the sensor to affect the ability of the sensor to process information. Examples of drugs and/or agents that can be used with the drug eluting substance 190 include a steroid. Examples of other substances that may suppress or prevent fibrotic growth are bisphosphonates, anti-platelet agents, such as aspirin, dipyridamole, ticlopidine, or sulfinpyrazone, and fibrinolytic agents such as plasmin, streptokinase, or urokinase. These agents may also be combined with heparin which is believed to provide immediate although temporary anticoagulation.

Figure 4:
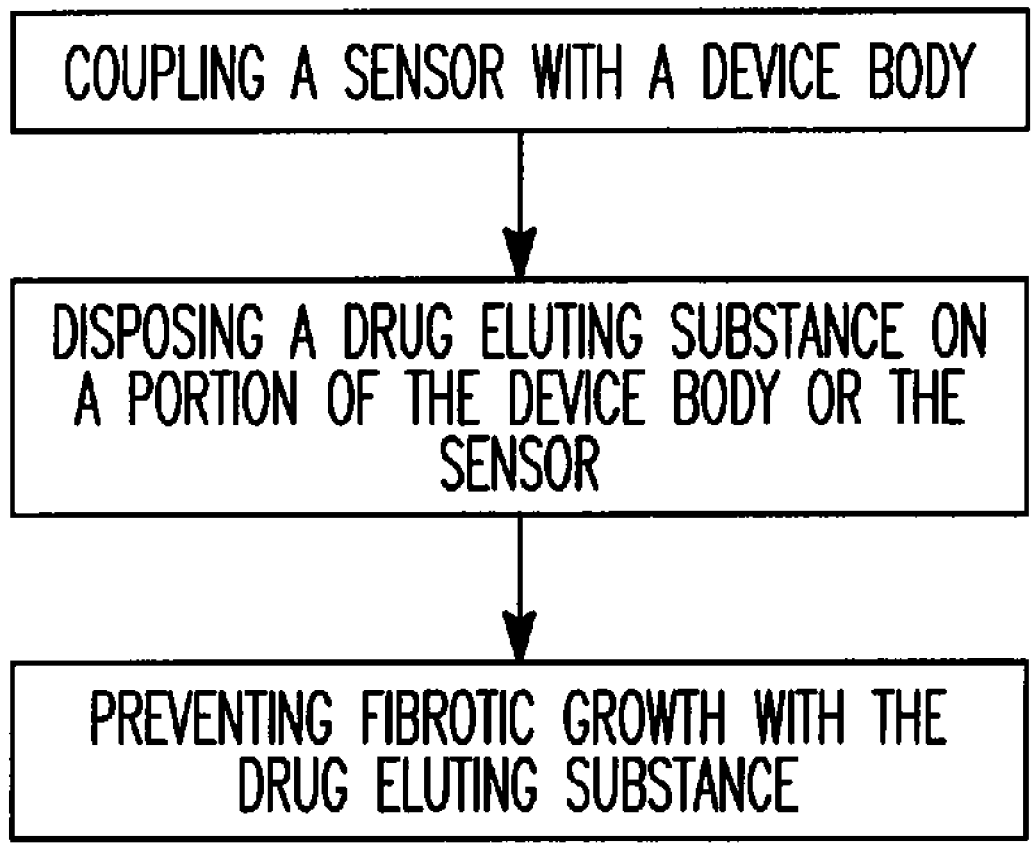
FIG. 4 is a flow diagram of a method in accordance with one embodiment.

A method, as illustrated in FIG. 4, includes providing a chronically implantable device body, coupling a chemical sensor with the implantable device body, disposing a drug eluting substance on a portion of the chronically implantable device body, and disposing the drug eluting substance on a portion of the chronically implantable device body includes disposing the drug eluting substance on, near, or directly adjacent to the chemical sensor. The method further includes preventing fibrotic growth with the drug eluting substance.

The drug eluting substance can be deposited on or near the sensor in several manners. For instance, in one option, disposing the drug eluting substance includes painting a drug on the chronically implantable device body. In another option, disposing the drug eluting substance includes filling a cavity of the chronically implantable device body with the drug eluting substance. In yet another option, the method further includes binding the drug eluting substance with a polymer, and optionally disposing the substance within the cavity.

Furthermore, the drug eluting substance can be formed in several different ways. For instance, in one option, the drug eluting substance is connected with a polymer. In another option, the method includes compressing a platelet inhibitor drug and forming a capsule, and disposing the capsule within a cavity of the chronically implantable device body.

In yet another option, the method includes compressing a drug with a starch and pressure molding the drug into a predetermined shape, and disposing the molded drug into a cavity of the chronically implantable device body. The method further includes, in another option, esterificating the drug eluting substance prior to disposing the drug eluting substance on, near, or directly adjacent to the chemical sensor. Other options include mixing a drug with liquid silicone to form the drug eluting substance, and further optionally curing the drug and liquid silicone after the drug and liquid silicone are disposed in one or more cavities of the chronically implantable device body. In yet one more option, the method further includes mixing a drug with a hydrogel to form the drug eluting substance. Examples of hydrogels include, but are not limited to polyacrylamide, polyvinylpyrolidone, polyhydroxyethal methacrylate, and polyvinyl alcohol.

The devices described and claimed herein will allow a consistent chronic performance of an implantable device, such as a transveous lead mounted sensor, allowing for optimization of therapy on a chronic basis. The drug eluting substance will reduce the fibrotic growth around or on the sensor, and will assist in facilitating the chronic performance of the sensors.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the invention should, therefore, be determined with reference to the appended claims, along with the full scope of equivalents to which such claims are entitled.

What is claimed is:

1. An apparatus comprising:
   an implantable device including at least one of a lead or a cardiac rhythm management device having a device body;
   one or more chemical sensors disposed on the device body; and
   a drug eluting coating disposed on the one or more chemical sensors, wherein the drug eluting coating prevents fibrotic growth on the one or more chemical sensors.

2. The apparatus of claim 1, wherein the drug eluting coating includes a drug mixed with one or more polymeric binders.

3. The apparatus of claim 1, wherein the drug eluting coating includes a drug eluting matrix that elutes one or more drugs over time.

4. The apparatus of claim 1, wherein the drug eluting coating includes an esterified drug.

5. The apparatus of claim 1, wherein the drug eluting coating includes a pre-compressed drug substance.

6. The apparatus of claim 1, wherein the one or more chemical sensors are coupled to a distal portion of the device body, the distal portion of the device body configured for insertion into a heart of a subject.

7. The apparatus of claim 1, wherein the drug eluting coating comprises a steroid.

8. The apparatus of claim 1, wherein the drug eluting coating comprises dexamethasone.

9. A method comprising:
   coupling a chemical sensor with a device body of a lead or a cardiac rhythm management device; and
   disposing a drug eluting coating on or directly adjacent to the chemical sensor, wherein the drug eluting coating prevents fibrotic growth on the chemical sensor.

10. The method of claim 9, wherein disposing the drug eluting coating includes painting a drug on an outer surface of at least one of the device body or the chemical sensor.

11. The method of claim 9, further comprising binding a drug with one or more polymers to form the drug eluting coating.

12. The method of claim 9, further comprising compressing a drug with a starch to form the drug eluting coating.

13. The method of claim 9, further comprising mixing a drug with a silicone liquid to form the drug eluting coating.

14. The method of claim 13, further comprising curing the drug and the silicone liquid.

15. The method of claim 9, further comprising mixing a drug with a hydrogel to form the drug eluting coating.

16. The method of claim 9, further comprising esterifying a drug to form the drug eluting coating prior to disposing the drug eluting coating at least one of on, or directly adjacent the chemical sensor.

17. An apparatus comprising:
- an implantable device including at least one of a lead or a cardiac rhythm management device having a device body;
- one or more chemical sensors disposed on the device body; and
- a drug eluting coating disposed directly adjacent the one or more chemical sensors, wherein the drug eluting coating prevents fibrotic growth on the one or more chemical sensors.

18. The apparatus of claim 17, wherein the drug eluting coating includes a drug mixed with one or more polymeric binders.

19. The apparatus of claim 17, wherein the drug eluting coating includes a drug eluting matrix that elutes one or more drugs over time.

20. The apparatus of claim 17, wherein the drug eluting coating includes an esterified drug.

21. The apparatus of claim 17, wherein the drug eluting coating includes a pre-compressed drug substance.

22. The apparatus of claim 17, wherein the drug eluting coating comprises a steroid.

23. The apparatus of claim 17, wherein the drug eluting coating comprises dexamethasone.

24. The apparatus of claim 17, wherein the drug eluting coating is coated on the device body.

25. The apparatus of claim 17, wherein the one or more chemical sensors are defined in part by a sensor outer perimeter, and the drug eluting coating is disposed around the sensor outer perimeter adjacent to the one or more chemical sensors.

* * * * *